United States Patent
Buxmann et al.

(10) Patent No.: US 10,165,785 B2
(45) Date of Patent: *Jan. 1, 2019

(54) PROCESS FOR PRODUCING A COMPOSITION FOR INCREASING MUSCLE MASS

(71) Applicant: MYOS RENS Technology Inc., Cedar Knolls, NJ (US)

(72) Inventors: Waldemar Buxmann, Hamburg (DE); Volker Heinz, Quakenbrueck (DE); Stefan Toepfl, Osnabrueck (DE)

(73) Assignee: MYOS RENS TECHNOLOGY INC., Cedar Knolls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/406,951

(22) Filed: Jan. 16, 2017

(65) Prior Publication Data

US 2017/0215442 A1 Aug. 3, 2017

Related U.S. Application Data

(63) Continuation of application No. 14/468,303, filed on Aug. 25, 2014, now abandoned, which is a continuation of application No. 13/765,340, filed on Feb. 12, 2013, now Pat. No. 8,815,320.

(30) Foreign Application Priority Data

Jun. 11, 2012 (EP) .................................. 12171561

(51) Int. Cl.
| | |
|---|---|
| A23B 5/015 | (2006.01) |
| A23B 5/03 | (2006.01) |
| A23B 5/00 | (2006.01) |
| A23L 3/015 | (2006.01) |
| A23L 5/30 | (2016.01) |
| A23L 15/00 | (2016.01) |
| A23L 3/32 | (2006.01) |
| A61K 35/57 | (2015.01) |
| A23P 10/30 | (2016.01) |
| A61K 38/17 | (2006.01) |
| C07K 14/47 | (2006.01) |
| A23D 9/013 | (2006.01) |
| A23P 10/40 | (2016.01) |
| A23L 33/17 | (2016.01) |

(52) U.S. Cl.
CPC ................ *A23B 5/015* (2013.01); *A23B 5/00* (2013.01); *A23B 5/03* (2013.01); *A23D 9/013* (2013.01); *A23L 3/015* (2013.01); *A23L 3/0155* (2013.01); *A23L 3/32* (2013.01); *A23L 5/30* (2016.08); *A23L 15/00* (2016.08); *A23L 15/20* (2016.08); *A23L 33/17* (2016.08); *A23P 10/30* (2016.08); *A23P 10/40* (2016.08); *A61K 35/57* (2013.01); *A61K 38/1709* (2013.01); *C07K 14/4703* (2013.01); *A23V 2002/00* (2013.01)

(58) Field of Classification Search
CPC .. A23B 5/00; A23B 5/03; A23B 5/015; A23L 15/20; A23L 5/30; A23L 3/32; A23L 3/0155; A23P 10/30; A61K 35/57; A23V 2002/00

See application file for complete search history.

(56) References Cited

U.S. PATENT DOCUMENTS

| | | | | |
|---|---|---|---|---|
| 6,726,951 B2* | 4/2004 | Campbell | .............. | A21D 2/262 426/471 |
| 8,815,320 B2* | 8/2014 | Buxmann | .............. | A23B 5/015 422/1 |
| 2005/0287260 A1* | 12/2005 | Efstathiou | ................ | A23B 5/00 426/326 |
| 2008/0003335 A1* | 1/2008 | Singh | ..................... | A23B 5/022 426/299 |
| 2008/0311259 A1* | 12/2008 | Singh | ..................... | A23B 5/015 426/330 |

OTHER PUBLICATIONS

CN101380069 Abstract and English Translation published Mar. 11, 2009.*
Yan et al. Eur. Food. Res. Technol. Published May 2010.*
Abstract for KR953183 published Apr. 2010.*

* cited by examiner

*Primary Examiner* — Anthony J Weier
(74) *Attorney, Agent, or Firm* — Licata & Tyrrell P.C.

(57) ABSTRACT

A process for producing a composition from a biological source, which composition is preserved and, especially pathogen free and is storage stable, preferably at room temperature. Embodiments of the invention provide a process for producing a composition from eggs.

9 Claims, No Drawings though likely contains the avian egg ingredient follistatin with its natural biological activity, and the ingredients of the liquid egg preparation, especially the unsaturated fatty acids and vitamins with their natural activities. Whereas irradiation, especially beta or gamma radiation, can be used as a step of preservation, it generates radicals from the ingredients of the egg, reducing the activity of follistatin and the amount of unchanged unsaturated fatty acids and of vitamins. The reaction products of these radicals can give the product an offensive smell and flavour, and are suspected to be detrimental to the consumer.

PROCESS FOR PRODUCING A COMPOSITION FOR INCREASING MUSCLE MASS

CROSS-REFERENCE TO RELATED APPLICATIONS

This application is a continuation of U.S. patent application Ser. No. 14/468,303, filed Aug. 25, 2014, which claims priority to U.S. patent application Ser. No. 13/765,340, filed Feb. 12, 2013, now U.S. Pat. No. 8,815,320, issued on Aug. 26, 2014, which claims priority from EP 12171561.9, filed on Jun. 11, 2012 at the European Patent Office, the disclosures of which are incorporated herein by reference in their entireties as if fully set forth herein.

BACKGROUND

Field of the Invention

Embodiments of the present invention related to a method for producing a composition for increasing muscle mass.

Related Art

Whereas the pasteurization of liquid egg yolk is shown to inactivate the biological activity of follistatin contained therein, it is described that freeze-dried emulsified egg yolk can be irradiated, e.g. by gamma radiation or by an electron beam for preservation.

SUMMARY

Embodiments of the present invention relates to a process for producing a composition for increasing muscle mass from a biological source, wherein the composition is preserved, storage stable at room temperature, and pathogen free. Upon ingestion, the composition has activity to support, induce and/or positively regulate the increase of muscle in humans and animals. The composition is therefore suitable for use as a food ingredient or nutrition additive for humans and animals, e.g. for use as a compound for improving muscle increase and/or muscle regeneration.

Preferably, the process for producing the composition, and the composition itself, are free from added chemical preservatives, most preferably, the process for producing the composition, and the composition, respectively, essentially consist of the natural components of the starting material, egg and its components, only subject to the physical treatment steps of the process.

DETAILED DESCRIPTION

Embodiments of the invention are directed to a process for producing a composition from avian eggs or its components, especially from egg yolk, egg white or whole egg, the process comprising the preservation while maintaining a temperature below 38° C., preferably below 20° C., more preferably below 10° C., which step of preservation comprises or consists of subjecting the liquid egg yolk to a pressure of at least 4000 bar, for at least 1 minute, preferably to 5500-6500 bar, more preferably to 6000 bar for at least 1 minute, preferably for 3 minutes, more preferably for at least 5 minutes, preferably using an adiabatic compression and pressure release, and/or pulsed electric field treatment, preferably in a continuous process while pumping the liquid egg or its components, especially egg yolk, egg white or whole egg, through the space limited by at least 2 discharge electrodes, e.g. generating an electric field strength of 5 to 40 kV/cm, e.g. at 12 kV/cm at a flow rate of the liquid egg yolk of 30 L/h at a temperature of 30° C., preferably using unipolar pulses having a pulse duration of 5 to 20 µs, preferably of 10 µs, at a repetition rate of 70 to 200 Hz, especially positive, rectangular pulses. At an energy input of 50 to 140 kJ/kg, the decrease in bacterial contamination, determined as CFU, was by a factor of 10 to 630, respectively.

The embodiments of the step of preservation are non-thermal process steps, i.e. an increase in temperature that may occur during the high pressure treatment and/or pulsed electric field treatment is not causative for the reduction in micro-organisms, especially of bacteria to achieve preservation. In addition, the embodiments of the step of preservation are physical treatment methods, i.e. without addition of antimicrobial chemical compounds. Accordingly, the embodiments of the step of preservation are non-thermal process steps consisting of physical treatment steps, which do not generate radicals and therefore maintain the chemical structure of the ingredients, especially of unsaturated fatty acids and vitamins of the composition.

It was found that the high pressure treatment and/or the pulsed electric field treatment of liquid whole egg, liquid egg white, or liquid egg yolk effectively reduces the bacterial contamination by a factor of at least 10, preferably by a factor of at least 100, more preferably of at least 1000. For example, for high pressure treatment, a reduction of the bacterial contamination to about 50 CFU/g, corresponding to a reduction by a factor of 3000 was found when starting from raw liquid egg yolk having a natural bacterial content of $1.5 \times 10^5$ CFU/g. For pulsed electric field treatment, a reduction by a factor of 10 to a factor of 1000 was found. The reduction of the natural microbiological contamination by the high pressure treatment and/or the pulsed electric field treatment is sufficient for preserving the egg white, whole egg or egg yolk.

Preferably, the process subsequent to the preservation step comprises drying, for example freeze-drying of the liquid egg preparation, especially egg yolk, egg white or whole egg, resulting in an egg containing powder, especially an egg yolk, egg white or whole egg containing powder, preferably in a powder consisting essentially of the high pressure treated and/or pulsed electric field treated egg or egg constituents, e.g. egg yolk, egg white or whole egg. In the alternative to freeze-drying, other suitable types of drying may be utilized. For example, the drying can be fluidized bed drying, preferably at a temperature at or below 42° C., preferably at or below 40° C., more preferably at or below 38° C. or at or below 35° C.

The process for producing the composition comprising a preservation step comprising or consisting of high pressure treatment and/or pulsed electric field treatment, preferably with subsequent drying, especially but not limited to freeze-drying, leads both to an efficient reduction of bacterial contamination as determined e.g. as viable bacteria, and to follistatin maintaining its biological activity, e.g. to at least 50%, preferably to at least 70%, more preferably to at least 80%, more preferably to at least 85%, at least 90% or to at least 95%.

Especially in view of preservation processes using irradiation, it is an advantage of the process of the invention that no radicals are generated by the step of preservation, and therefore the resulting preserved liquid egg yolk, egg white or whole egg, which preferably is subsequently dried, preferably freeze-dried, contains less or no radicals and reaction products of radicals. E.g. the preserved liquid egg yolk, egg white or whole egg, as well as the dried, preferably freeze-dried, preserved egg yolk, egg white or whole egg, contains unsaturated fatty acids of the egg yolk essentially in their natural state and composition, e.g. without changes to their double bonds. Accordingly, the composition obtainable by the process of the invention preferably contains the unsaturated fatty acids of egg yolk without changes of their double bonds, i.e. in their natural biological constitution.

In the alternative to whole egg or egg yolk, the white of egg can be used in the process.

Preferably, in the process, no chemical preservative is added, e.g. no antimicrobial agent is added. Optionally, an antioxidant is added, e.g. ascorbic acid or a neutral salt thereof. Preferably, the whole egg, egg white, more preferably egg yolk only is free from added ingredients, e.g. the whole egg, egg white, or more preferably the egg yolk, is subjected to the physical process steps only, which comprise, preferably consist of subjecting liquid whole egg, egg white or liquid egg yolk to high pressure treatment and/or to pulsed electric field treatment, preferably followed by drying, e.g. freeze-drying or fluidized bed drying.

For high pressure treatment, it is preferred that the liquid whole egg, white of egg or liquid egg yolk is contained in sealed containers having an elastic wait e.g. in plastic bags, more preferably free from gas, more preferably degassed. For a gas-free whole egg, egg white or liquid egg yolk in a container, gas bubbles can be expelled before sealing the container. For degassing, a reduced pressure can be applied prior to high pressure treatment, preferably also prior to pulsed electric field treatment.

High pressure treatment is generally carried out using water as a compression medium that is pumped into a sealed chamber containing the liquid whole egg, egg white or liquid egg yolk until the high pressure is reached, maintaining the high pressure, and then releasing the pressure, e.g. by opening the high pressure container.

It was found that after high pressure treatment within sealed containers, e.g. in sealed polyethylene bags, the liquid whole egg, egg white or liquid egg yolk preparation is stable, e.g. for 12 to 24 hours, preferably for 2 to 5 days, e.g. at 5 to 10° C., without a drastic increase in bacterial contamination, and especially without a significant loss of follistatin activity.

For high pressure treatment, the adiabatic increase in temperature due to the high pressure preferably is counteracted by cooling the liquid whole egg, egg white or liquid egg yolk to a temperature which is at least 5° C., preferably about 10° C. below the maximum temperature, e.g. below 38° C. prior to the treatment. Preferably, prior to high pressure treatment and/or prior to the pulsed electric field treatment, the liquid whole egg, egg white or liquid egg yolk is cooled to a temperature of between 0 and 28° C., preferably to 5 to 20° C., more preferably to a maximum of 10° C.

For pulsed electric field treatment, it was found that a short rise in temperature, e.g. to a maximum of 45° C., preferably to a maximum of 42° C. or to 40° C., for maximally 10 s, preferably for maximally 5 or maximally 2 s results in a low loss of active follistatin. Accordingly, for the pulsed electric field treatment, the aforementioned short rise in temperature is acceptable, although less preferred.

Active follistatin was determined by size separation, e.g. by size-exclusion HPLC or by SDS-polyacrylamide gel electrophoresis (SDS-PAGE), optionally followed by Western blotting and immunospecific detection using an anti-follistatin antibody. A reduction of the size-specific signal identified for follistatin in eggs was used as an indicator for the reduction of follistatin activity, because an inactivation of follistatin results in the change, e.g. reduction of the molecule size.

The process may comprise a step of concentrating the whole egg, egg white or egg yolk of eggs. For concentrating, the fraction of whole egg, of egg white or of egg yolk having the higher proportion of follistatin is used, the fraction being obtained e.g. by size separation or by density separation. The preferred fraction is the fraction containing the egg yolk membrane, e.g. obtained from separating egg yolk or whole egg, and the fraction containing chalazae, e.g. obtained from separating the white of egg or whole egg. Preferably, the preferred fraction contains the major portion of the egg yolk membranes and/or of the chalazae of the whole egg, egg white or egg yolk subjected to the concentrating or separating step. For separating by size separation, sieving can be used, e.g. of a mesh size of 0.5 mm to 2 mm, preferably approx. 0.5 to 1 mm. Using size separation, the preferred fraction is the egg yolk membrane and/or chalazae containing fraction, which is the particulate or large fraction. For separating by density separation, centrifugation, e.g. using a centrifugal separator. Using density separation of whole egg, egg white or egg yolk, the higher density fraction is the preferred fraction.

Optionally, prior to the step of concentrating the whole egg, egg white or egg yolk of the eggs by separating the fraction containing the egg yolk membrane and/or chalazae, the whole egg, egg white or egg yolk can be diluted to facilitate the separating step, e.g. using water as a diluent, the water optionally containing salt.

In the alternative or in addition to whole egg, egg white or egg yolk of eggs, the process can be performed using blood serum from slaughtered animals as the starting material. Accordingly, the blood serum can replace the whole egg, egg white or egg yolk in the process, and therefore the description relating to whole egg, egg white or egg yolk also refers to blood serum.

Optionally, the process can comprise the further step of mixing or encapsulating the dried preserved egg or egg constituent. Preferably, for mixing or encapsulating, the dried egg yolk, whole egg or egg white, or alternatively the dried blood serum, is admixed with a solution, preferably an aqueous solution of an encapsulating agent. The encapsulating agent can e.g. be a sugar, sugar alcohol and/or sugar polymer, a solution of which in the process is admixed with the preserved and dried egg yolk, whole egg or egg white, or alternatively the dried blood serum, and dried to produce encapsulated dried egg yolk, whole egg or egg white, or alternatively the dried blood serum. The sugar can e.g. be sucrose, fructose, glucose, and/or corn syrup. The sugar alcohol can e.g. be maltitol, isomalt etc. The sugar polymer can e.g. be starch, modified starch and/or cellulose and/or methylcellulose, which preferably also serves as an anti-caking agent.

As a specific advantage of the high pressure treatment of liquid egg yolk, whole egg or egg white, it has been found that the bioavailability and digestibility of the protein, preferably of the total protein, is enhanced. Therefore, the process comprising the step of high pressure treatment of liquid egg yolk, whole egg or egg white is preferred for producing a preserved composition containing biologically active follistatin, in which composition the protein has increased bioavailability, e.g. increased digestibility, for example in relation to the non-treated liquid egg yolk, whole egg or egg white.

Several embodiments of the invention are now illustrated non-limiting experimental examples.

Example 1

Production of Preserved Egg Yolk Containing Active Follistatin

Hen eggs contained from a certified breeding station were used, which eggs were not brooded. The eggs were cracked and separated into egg yolk and the white of egg automatically. As raw liquid egg yolk, 3000 L egg yolk were used that were preferably homogenized by stirring were maintained at 5 to 10° C. and filled under sterile conditions into polyethylene bags and sealed after expulsion of entrapped air bubbles. These polyethylene bags could have a volume of between 1 L and 50 L, preferably of 5 to 20 L each. The bags were arranged in a high pressure chamber (NC-Hyperbaric, Spain). Using water as a pressurizing medium, the pressure was increased to 6000 bar within 10 to 20 minutes. After a holding time of 3 or 5 minutes, respectively, the pressure was released by opening a release valve.

The bacterial contamination was determined by standard dilution plating on complete medium and counting following cultivation in an incubator at 37° C. for 48 h.

Aliquots from the high pressure treated egg yolk were kept at about 5° C. for a few hours and subsequently freeze-dried by freezing the egg yolk and applying vacuum to withdraw water, while controlling the temperature of the egg yolk to preferably not exceed 10° C., preferably 5° C., preferably keeping the egg yolk in a frozen state.

The microbiological analysis showed that the high pressure treatment both for 3 minutes and 5 minutes resulted in a drastic reduction of bacterial contamination, and also the subsequent step of freeze-drying further reduced the bacterial contamination.

TABLE 1 bacterial contamination, measured as CFU/g

| sample | Salmonella in 25 g sample | Total cell count (CFU/g) |
|---|---|---|
| raw liquid egg yolk | Negative | $1.5 \times 10^5$ |
| liquid egg yolk after 6000 bar, 3 min | Negative | 50 |
| liquid egg yolk after 6000 bar, 5 min | Negative | 50 |
| freeze-dried egg yolk after 6000 bar, 3 min | Negative | 40 |
| freeze-dried egg yolk after 6000 bar, 5 min | Negative | <10 |

CFU = colony forming units (viable micro-organisms)

Follistatin activity in the liquid egg yolk as determined by SDS-PAGE showed a reduction by approx. 15%, or a content of 85% active follistatin, on the basis of the content of active follistatin as determined by SDS-PAGE in the raw liquid yolk.

In the freeze-dried egg yolk, the content of active follistatin in relation to the total protein concentration was the same as in the liquid egg yolk after high pressure treatment. This shows that the step of freeze-drying does not substantially affect the activity of follistatin, e.g. freeze-drying does not substantially reduce the concentration of active follistatin per total protein content.

Example 2

Fraction of Freeze-Dried Egg Yolk Containing Active Follistatin Using Pulsed Electric Field Treatment An aliquot of the raw liquid egg yolk used in Example 1 was treated at a flow rate of 30 L/h at 30° C. by pulsed electric field of a field strength of 12 kV/cm using unipolar positive pulses having a pulse duration of 10 µs at a repetition rate of 200 Hz. At an energy input of 50 to 140 kJ/kg, the viable bacterial contamination was reduced by a factor of 10 and 630 CFU, respectively, as determined by dilution plating.

Using SDS-PAGE, a reduction of active follistatin by approx. 15%, or a residual activity of follistatin of 85% based on the raw egg yolk was found. No thermal denaturation of the liquid egg yolk was observed in SDS-PAGE.

Example 3

Concentrating Whole Egg, White of Egg or Egg Yolk by Separation

The process of Example 1 was repeated with the alteration that before the high pressure treatment the egg yolk was separated by centrifugation at 3343×g for 20 min into a high density fraction that was collected as a pellet and a low density supernatant fraction. The high density was found the high follistatin fraction.

In the alternative, whole egg or white of egg was separated by centrifugation at 3343×g for 20 min into a high density fraction that was collected as a pellet and a low density supernatant fraction. Again, the high density was found the high follistatin fraction.

The analysis of the follistatin content is shown below:

| fraction | Follistatin [µg/kg] |
|---|---|
| white of egg, prior to centrifugation | 15 |
| white of egg, pellet | 33 |
| whole egg, prior to centrifugation | 23 |
| whole egg, pellet | 41 |
| egg yolk, prior to centrifugation | 4 |
| egg yolk, pellet | 36 |

These results show that the separation of egg yolk, whole egg or egg white to a higher density fraction, corresponding to egg yolk membranes and chalazae, results in an increased concentration of follistatin, which fraction after the step of preservation, preferably with subsequent drying, yields a composition having an increased follistatin concentration.

Preferably, the egg yolk, whole egg or egg white prior to the separation was not homogenized, e.g. the egg yolk, whole egg or egg white was passed through a wide sieve or was stirred to only crack the egg yolk membrane to allow egg yolk to exit, preferably without breaking the egg yolk membrane or chalazae into small pieces.

Various features of the invention are set forth in the appended claims. While the foregoing is directed to embodiments of the present invention, other and further embodiments of the invention may be devised without departing from the basic scope thereof. It is also understood that various embodiments described herein may be utilized in combination with any other embodiment described, without departing from the scope contained herein.

What is claimed is:

1. A process for producing a composition for increasing muscle mass, said process comprising:
providing raw liquid egg yolk, raw liquid whole egg or raw liquid egg white originating from eggs, diluting with a diluent and then concentrating the raw liquid egg yolk, raw liquid whole egg or raw liquid egg white to a fraction containing the egg yolk membrane and/or the chalazae, and subjecting the concentrated fraction to a step of preservation while maintaining the temperature at or below 38° C., wherein the step of preservation is selected from subjecting the raw liquid egg yolk, raw liquid whole egg or raw liquid egg white to a high pressure treatment of at least 4500 bar for at least 1 min, from subjecting the raw liquid egg yolk, raw liquid whole egg or raw liquid egg white to a pulsed electric field treatment of at least 5 kV/cm at a flow rate of 30 L/h, and from a combination of the high pressure treatment and the pulsed electric field treatment to provide a preserved liquid egg yolk, preserved liquid whole egg or preserved liquid egg white so that a composition for increasing muscle mass is produced.

2. The process according to claim 1, wherein the step of preservation consists of the high pressure treatment, wherein the raw liquid egg yolk, raw liquid whole egg or raw liquid egg white is filled into containers, the containers are sealed and subjected to the high pressure treatment.

3. The process according to claim 1, comprising drying the preserved liquid egg yolk, preserved liquid whole egg or preserved liquid egg white subsequent to the step of preservation.

4. The process according to claim 3, wherein drying includes at least one of freeze-drying and fluidized bed drying.

5. The process according to claim 1, wherein the step of providing comprises opening eggs and separating the egg yolk from the white of egg.

6. The process according to claim 1, comprising cooling the raw liquid egg yolk, raw liquid whole egg or raw liquid egg white to a maximum temperature of 10° C. prior to the step of preservation.

7. The process according to claim 1, comprising degassing the raw liquid egg yolk, raw liquid whole egg or raw liquid egg white prior to the step of preservation.

8. The process according to claim 1, wherein the fraction containing the egg yolk membrane and/or the chalazae is a high density fraction obtained by centrifugation and/or a larger size fraction obtained by size separation.

9. The process according to claim 1, wherein subsequent to the step of preservation, the preserved liquid egg yolk, preserved liquid whole egg or preserved liquid egg white is dried and subsequently admixed with a solution of a sugar, a sugar alcohol and/or a sugar polymer and dried for encapsulating the egg yolk, whole egg or egg white.

* * * * *